United States Patent [19]

Tech et al.

[11] 4,337,791
[45] Jul. 6, 1982

[54] FLOW REGULATOR ASSEMBLY

[75] Inventors: James H. Tech, Battle Creek; Mary J. LaFountain, Marshall, both of Mich.; Virginia M. Van Sickle, Glen Ellyn, Ill.

[73] Assignee: La-Van Tech Development Corp., Marshall, Mich.

[21] Appl. No.: 207,129

[22] Filed: Nov. 17, 1980

[51] Int. Cl.³ ............................................. F16K 7/06
[52] U.S. Cl. ...................................... 137/556; 251/6; 251/297; 251/8
[58] Field of Search ................ 251/6, 8, 297; 137/556

[56] References Cited
U.S. PATENT DOCUMENTS

| | | | |
|---|---|---|---|
| 653,629 | 7/1900 | Schneider | 251/6 |
| 2,595,511 | 5/1952 | Butler | 251/6 |
| 3,984,081 | 10/1976 | Hoganson | 251/6 |
| 4,238,108 | 12/1980 | Muetterties | 251/6 |

*Primary Examiner*—H. Jay Spiegel
*Attorney, Agent, or Firm*—Fisher, Gerhardt, Crampton & Groh

[57] ABSTRACT

A flow regulator assembly for controlling fluid flow in flexible tubes which can be attached at a point intermediate the ends of the tube and which has a regulating member rotatable to a selected position to move into engagement and deflect the tube to decrease fluid passage therein in proportion to the amount of rotation of the regulating member. Means are provided to resist rotation of the regulating member from its selected position and provision is made for an indicator which makes it possible to select the rate of flow visually or through a sense of feel. One embodiment provides for selection of the rate of flow by listening to sounds made during rotation of the regulating member.

4 Claims, 12 Drawing Figures

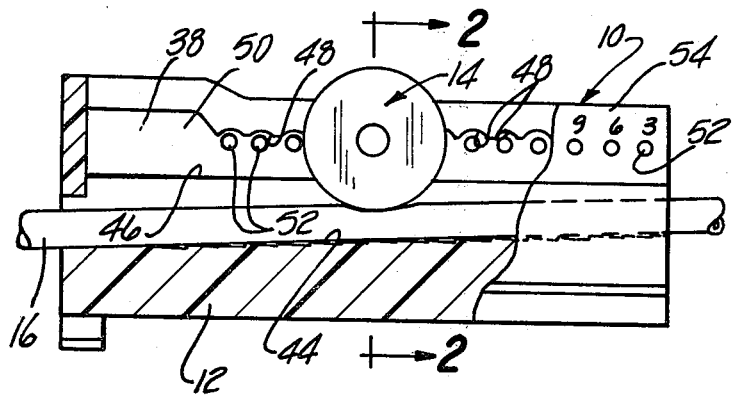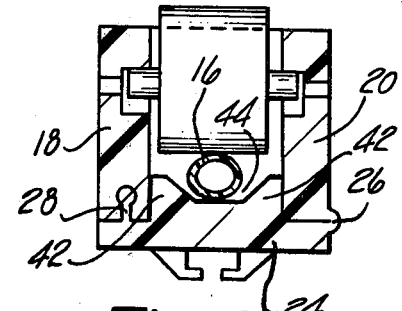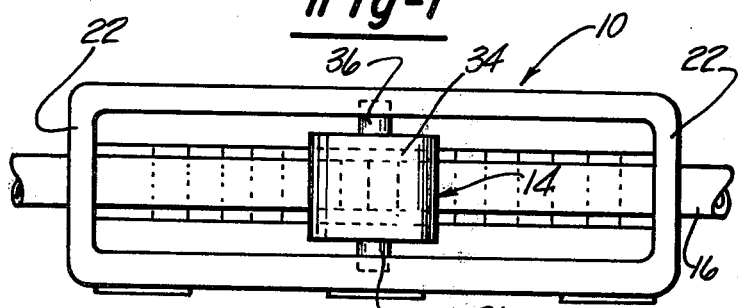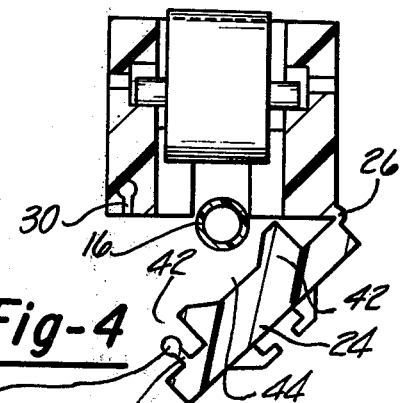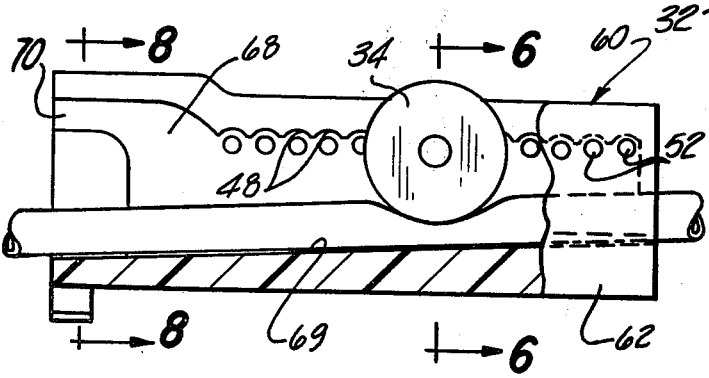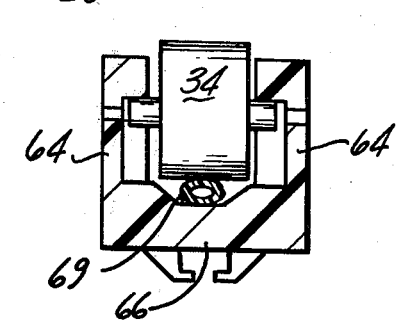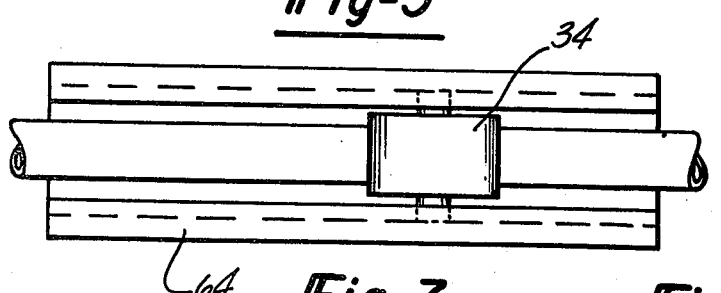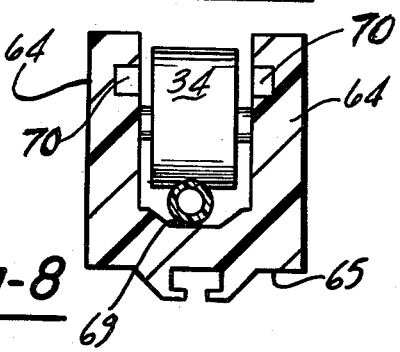

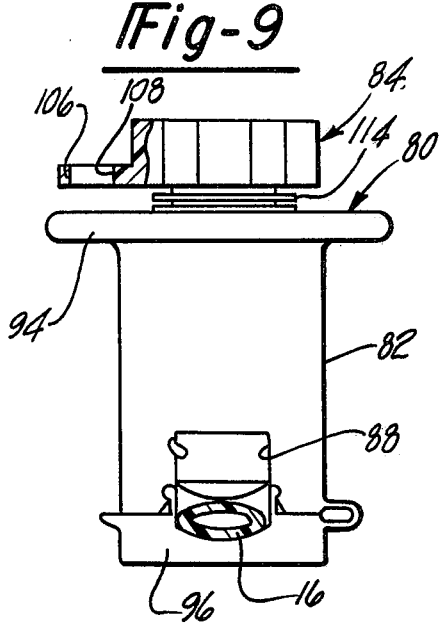
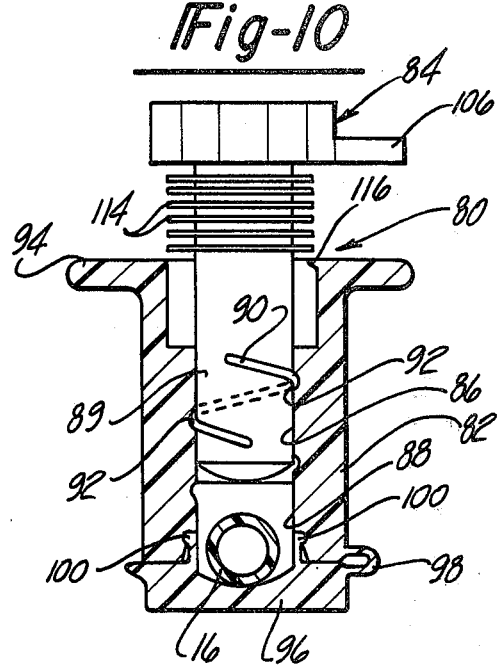
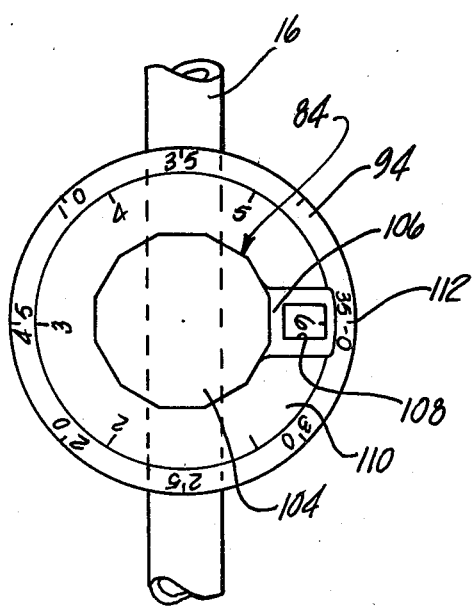
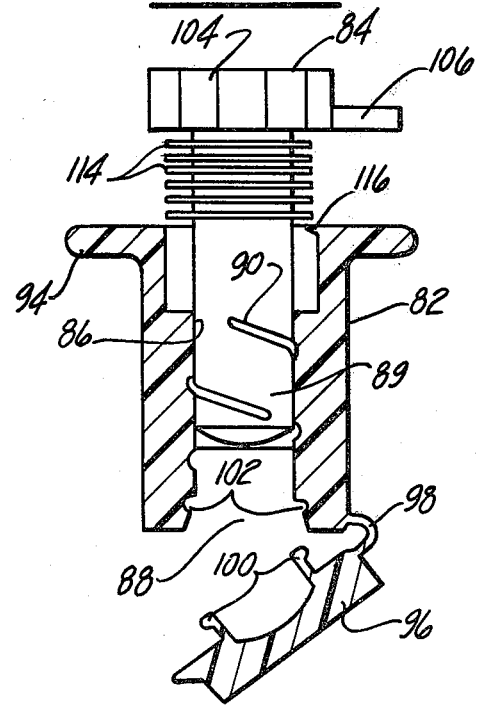

FLOW REGULATOR ASSEMBLY

The present invention relates to regulating the flow of fluid through a flexible tube and more particularly to a clamp arrangement for tubes of the type used for administering fluids parenterally to patients or in laboratories.

Various arrangements have been provided for regulating fluid flow in flexible tubes. Typically fluids in hospitals are administered by means of gravity flow from a container through a flexible tube to a hypodermic needle. It is important that various fluids be administered at a regulated, certain rate. Despite the various fluid flow devices available, the procedure as usually carried out requires the use of a second hand on watch and observing the rate of flow by counting the drops per minute passing through a sight tube into a dripchamber.

It is desirable that such flow regulating devices can be adjusted at least preliminarily by means other than actually employing a watch, and also to have the flow regulating device which can be attached to a tube at any intermediate point between its ends even when one end is attached to a source of medication and the other end is attached to a hypodermic needle.

It is an object of the invention to provide a flow regulator assembly which can be attached to an intermediate point of a flexible tube for adjustment to select the rate of fluid flow.

Another object of the invention is to provide a flow regulator assembly in which the rate of flow can be selected by determining the position of the control or regulating member by sensing its position visually, by feel or audibly.

The objects of the invention are accomplished by a flow regulator assembly which controls fluid flow in flexible tubes and includes a body member having a surface for engaging one side of a flexible tube and a regulating member rotatable to a selected position to move into engagement with the tube and to press it against the surface to restrict passage of fluid in the tube in proportion to the amount of rotation of the regulating member. The regulating member and body member have means which are engageable with each other to resist rotation of the regulating member to secure it in its selected adjustment position. Indicator means also are provided by which the position of the regulating member can be viewed or can be sensed through the fingers during the time the adjustment is being made. In one embodiment of the invention, the selected position also can be sensed by listening to the sound made during movement of the regulating member. All three of the disclosed embodiments make provision for attaching the flow regulator assembly to an intermediate point of a flexible tube.

These and other objects of the invention will be apparent from the following description of the various embodiments of the invention and from the drawings in which:

FIG. 1 is a view, partly in cross section, of the flow regulator assembly embodying the invention;

FIG. 2 is a cross sectional view taken on line 2—2 in FIG. 1;

FIG. 3 is a top view of the arrangement seen in FIG. 1;

FIG. 4 is a view similar to FIG. 2 but showing another position of operation of the flow regulator assembly;

FIG. 5 is a cross sectional view similar to FIG. 1 but showing another embodiment of the invention;

FIG. 6 is a cross sectional view taken on line 6—6 in FIG. 5;

FIG. 7 is a top view of the embodiment seen in FIG. 5;

FIG. 8 is a cross sectional view taken on line 8—8 in FIG. 5;

FIG. 9 is a side elevation of still another embodiment of the invention;

FIG. 10 is a cross sectional view of the arrangement in FIG. 9;

FIG. 11 is a top plan view of the embodiment seen in FIG. 9; and

FIG. 12 is a cross sectional view similar to FIG. 10 but showing the flow regulator assembly prior to attachment to a tube.

Referring to the drawings and particularly to FIGS. 1 through 4, a flow regulator assembly embodying the invention and designated generally at 10, includes a body member 12 which serves to hold and guide a regulating member 14 for rolling movement relative to a flexible tube 16 in which fluid flows.

In both embodiments of the invention illustrated in FIGS. 1 through 8, adjustment of the roller 34 to a selected position can be accomplished visually by observing the end of the shaft 36 in a selected one of the windows 52. To facilitate such visual selection of the position of the roller 34, the ends of the shaft 36 may be of a contrasting color to the body member 12 or if preferred, the entire regulating member 14 can be molded of plastic material different in color than the body member 12.

In making the adjustment the axle 36 is seated in the seats 48. As the roller is moved from one seat 48 to the adjacent seats 48, the change in position can be sensed in the finger of the person making the adjustment making it possible to make at least a preliminary adjustment without visual attention.

The length of the path of movement of the regulating member 14 determines the amount of pressure or squeezing action applied to the tube 16 and therefore the amount of liquid flow.

The body member 12 is molded in a single piece of plastic material. The body member 12 is generally box shaped with sidewalls 18 and 20 joined by end walls 22 seen in FIG. 3. The sidewalls 18 and 20 are also held in spaced apart relationship by a bottom portion 24 joined to the side wall 20 by a live hinge 26 molded integrally with the wall 20 and the bottom portion 24. The live hinge 26 permits the bottom portion 24 to be moved between the open position see in FIG. 4 and the permanently closed position seen in FIG. 2. In the closed position the bottom portion 24 is held in latched position relative to the wall 18 by a rib 28 adapted to be received in the slot 30 formed in wall 18. The rib 28 is formed with an enlarged head portion 32 which seats in a complementary portion of the slot 30 to permanently hold the bottom portion 24 in a latched position.

The regulating member 14 also is formed of plastic material and is in the form of a roller 34 having an integral axle 36 which extends from opposite ends of the roller 34. The opposite ends of the axle 36 are received in longitudinally extending and facing recesses 38 formed in the interior surfaces of the walls 18 and 20.

The bottom portion 24 is provided with a guide for the tube 16 formed by sidewalls 42 between which is an inclined surface 44 that engages one side of the tube 16 when the latter is in position within the body member 12.

The recesses 38 are mirror images of each other and each includes a straight bottom wall 46 and an upper wall made up of a plurality of semicircular seats 48 positioned adjacent to each other to extend generally parallel to the bottom wall 46. The seats 48 are of a size to receive the ends of axle 36 of the regulating member 14. The row of seats 48 are arranged to converge from left to right as viewed in FIG. 1 with the inclined surface 44.

In use the tube 16 may have one end already connected to a supply of liquid such as a medication, for example, and the other end of the tube may be connected to a receiver such as a needle, for example. The flow regulator 10 is adapted for mounting to a selected location on the tube 16 intermediate its ends by having the bottom portion 24 in the open position as viewed in FIG. 4. In that position, the body member holds the regulating member 14 so that the assembly can be moved into position over the tube 16. Thereafter the bottom portion can be hinged to a closed position so that the rib 28 enters the slot 30 and holds the bottom portion 24 securely in position relative to the remainder of the body portion. With the tube 16 disposed between the inclined surface 44 and the roller 34, a squeezing action can be applied to the flexible tube 16 to vary the cross sectional area and therefore the flow of fluid which in typical applications flows by the force of gravity. With the axle 36 positioned in the vertically enlarged portion of the recess 38 indicated at 50, the tube is not deflected and the full cross section is available for full liquid flow. As the regulating member is rotated progressively from one pair of aligned seats 48 to another, the tube 16 is progressively squeezed and progressively restricted increasing the amount of distance used for flow control. The amount of restriction can be gauged by viewing the end of the axle 36 through openings or windows 52 associated with each of the seats 48 at opposite ends of the axle 36. Each window may have indicia such as that indicated generally at 54 to indicate the liquid flow in terms of drops per minute or the time in hours to deplete the source of liquid. In the preferred embodiment of the invention one of the walls, such as wall 20, can be provided with indicia related to the rate of flow in drops per minute and the windows in the wall 18 can be used to indicate the total time to deplete a specific source.

Referring now to FIGS. 5 through 8, another embodiment of the invention is shown in which a flow regulator 60 has a body member 62 with sidewalls 64 joined together by an integeal bottom wall 66. The body member 62 can be considered to be generally channel shaped with no end walls or top wall.

The side walls 64 each have recesses 68 that face each other to receive a roller 34 identical with the roller used in the prior embodiment. The recesses 68 are provided with seats 48 and windows 52 arranged identically with the prior embodiment, that is, in generally converging relationship as considered from left to right in FIG. 5 relative to a bottom surface 69 in contact with the tube 16.

The ends of the recesses 68 as viewed in FIG. 5 are open to the end of the body member 62 by way of gate portions 70 to permit removal of the roller 34 completely from the remainder of the body member 62.

The flow regulator 60 is used in a manner similar to the prior embodiment except that attachment to the tube 16 is accomplished by first removing the roller 34 through gates 70 after which the body member 62 can be placed in position over the tube 16 and the roller 34 can be inserted through the gates 70 to enter the recesses 68. Thereafter the arrangement can be operated in a manner identical to the prior embodiment.

Referring now to FIGS. 9 through 12, still another embodiment of the invention is shown in which a flow regulator assembly 80 has a generally cylindrical body member 82 supporting a regulating member 84.

The body member 82, FIG. 10, has a bore 86 and an opening 88 which extends transversely to the bore 86. The bore 86 supports the regulating member 84 which is rotatable in the bore 86. The regulating member 84 has a stem portion 89 which is provided with a male thread 90 which is disposed in a mating female thread or groove 92. The pitch of the thread 90 and the groove 92 is such that a single rotation of the regulating member 84 operates to move the stem 89 axially of the bore 86 through its full range of movement which is slightly larger than the inside diameter of the tube 16 to be used with the flow regulator 80. One end of the body member 82 is provided with an annular flange 94 and the opposite end is provided with a lid or wall portion 96 joined integrally with the remainder of the body member 82 by a live hinge 98. The entire body member 82 including the lid or wall 96 and live hinge 98 are molded of a single unitary piece of plastic. Latch means in the form of a pair of prongs 100 are adapted to flex and to be permanently seated in complementary recesses 102 to securely hold the lid or wall 96 in locked position. In the open position seen in FIG. 12 the lid or wall 96 is sufficiently separated from the opening 88 so that the tube 16 can be inserted after which the lid or wall 96 is moved to its permanently closed position.

The upper end of the stem 89 of the regulating member 84 is provided with a knob 104 which forms a handle for rotating the stem 89. Projecting radially from one side of the knob 104 is an indicator 106. The indicator 106 has an opening or a window 108 through which indicia on an annulus indicated at 110 can be viewed. The end of the indicator 106 also can be in alignment with indicia on another annulus indicated at 112. The indicia at 110 can indicate the time in hours which will be required to deplete a specified supply of medication or liquid whereas the indicia at 112 can indicate the rate of flow such as drops per minute.

The upper end of the stem 89 is provided with a plurality of uniformly spaced annular rings 114. During axial movement of the regulating member 84 the annular rings 114 interfere with a tab 116 formed integrally with the body member 82 at the flange end of the bore 86. The annular rings 114 and tab 116 not only secure the regulating member 84 in the adjusted position but also make a clicking sound during adjustment to form an audible indicator of the axial position of the stem 89 within the bore 86 and therefore the amount of deflection of the liquid tube 16 and consequently the rate of flow.

In use, the flow regulator 80 can be placed at any intermediate point on a tube 16 by having the wall 96 in its open position as seen in FIG. 12 and by placing the opening 88 over the tube 16 and subsequently hinging the wall 96 so that the prongs 100 become seated in the recesses 102. Thereafter the regulating member 84 can be rotated to a selected position to obtain the desired rate of liquid flow.

Adjustment of the regulating member 84 will normally begin with the regulating member 84 at one end of its range, that is, in a position to permit the tube 16 to be fully open. Movement of the regulating member 84 can be made visually by moving the indicator 106 to a position which is selected visually. Adjustments can be selected at least preliminarily if desired, without the visual attention by counting the number of clicks resulting from interference of the rings 114 with the tab 116 during rotation of knob 104. Even in the absence of sound or light the adjustment also can be sensed by the fingers due to the increase in resistance as each ring 114 passes the tab 116.

A flow regulator for controlling fluid flow in flexible tubes has been provided which can be added to a tube at an intermediate point without requiring threading the tube from one end. The flow regulator assemblies of the disclosed embodiments permit regulation of fluid flow in the flexible tube by rotating a regulating member to selected positions with the amount of rotation determining the degree of fluid flow. The flow regulators are provided with indicator means by which it is possible to select a predetermined position for the regulating member to determine the rate of flow visually or by sensing the extent of adjustment in the fingers of the hand. In one embodiment of the invention it can be selected audibly. The flow regulator assembly also provides means for resisting movement of the regulating member from its selected position once an adjustment has been made.

The embodiments of the invention in which an exclusive property or privilege is claimed are defined as follows:

1. A flow regulator assembly for controlling fluid flow in flexible tubes comprising: a body member having parallel spaced side walls spaced to opposite sides of a wall portion having a surface for engaging one side of a flexible tube, a roller member having an axle extending from opposite ends of said roller, the ends of said axle being disposed in elongated and facing recesses formed in the interior surfaces of said side walls to maintain said roller attached to said body member, said surface of said wall portion and said elongated recesses being disposed at an angle to each other, said roller being rotatable to move said axle to selected positions in said recesses and to move said roller into engagement with the tube and depress the tube against said surface to restrict the passage in the tube in proportion to the amount of rotation of said roller member, means formed in said recesses and engageable with said axle of said roller member to resist rotation of said roller member from said selected position, indicator means indicating the position of said roller member and the corresponding fluid flow in said tube, hinge means formed as a unit with said wall portion and one of said side walls to permit movement of said wall portion from an open position permitting attachment of said body member to a selected point intermediate opposite ends of the tube to position said tube between said roller member and said surface, and means for latching said wall portion to the other of said side walls when said wall portion is in a closed position after said tube has been disposed in said body member, said body member, said wall portion, said hinge means and said latch means being molded as a unit of plastic material.

2. The flow regulator according to claim 1 wherein said indicator means includes indicia on said body member and wherein said roller member has an indicating element alignable with said indicia.

3. The flow regulator assembly of claim 1 wherein said means to resist rotation are a plurality of semi-circular seats positioned adjacent to each other formed in said body member to receive said axle of said roller member.

4. The flow regulator assembly of claim 1 wherein said latching means is a rib adapted to be received in a slot formed in said sidewall, said rib having an enlarged head portion which seats in a complementary portion of said slot to hold said wall portion in a latched position.

* * * * *